(12) United States Patent
Myhling

(10) Patent No.: US 6,328,991 B1
(45) Date of Patent: *Dec. 11, 2001

(54) COMPOSITION AND METHOD FOR PREVENTION OF SEXUALLY TRANSMITTED DISEASES, INCLUDING AIDS

(76) Inventor: John Myhling, P.O. Box 141, Rhinebeck, NY (US) 12572

( * ) Notice: Subject to any disclaimer, the term of this patent is extended or adjusted under 35 U.S.C. 154(b) by 0 days.

This patent is subject to a terminal disclaimer.

(21) Appl. No.: 09/451,362

(22) Filed: Nov. 30, 1999

Related U.S. Application Data

(63) Continuation-in-part of application No. 08/140,794, filed on Oct. 21, 1993, now Pat. No. 5,527,534, which is a continuation-in-part of application No. 07/964,494, filed on Oct. 21, 1992, now abandoned.

(51) Int. Cl.⁷ ............... A61F 6/06; A61F 6/14; A61M 31/00

(52) U.S. Cl. ................. 424/430; 424/DIG. 15; 514/841; 514/843; 514/960; 514/975; 128/830; 128/832; 128/833; 604/55

(58) Field of Search .............. 424/430, DIG. 15; 514/841, 843, 967, 975; 128/830, 832, 833; 604/55

(56) References Cited

U.S. PATENT DOCUMENTS 5,070,889 * 12/1991 Leveen et al. .......... 128/830
5,527,534 * 6/1996 Myhling .................. 424/430

\* cited by examiner

Primary Examiner—Carlos A. Azpuru
(74) Attorney, Agent, or Firm—Levisohn, Lerner, Berger & Langsam

(57) ABSTRACT

A chemical composition, method and product for administration into the vaginal canal. The composition, method and product are effective in preventing the spread of sexually transmitted diseases, including the spread of AIDS.

27 Claims, 3 Drawing Sheets

US 6,328,991 B1

COMPOSITION AND METHOD FOR PREVENTION OF SEXUALLY TRANSMITTED DISEASES, INCLUDING AIDS

RELATED APPLICATIONS

This application is a continuation-in-part of U.S. application Ser. No. 08/140,794, filed Oct. 21, 1993 and issuing as U.S. Pat. No. 5,527,534 on Jun. 18, 1996, which is a continuation-in-part of U.S. application Ser. No. 07/964,494 filed Oct. 21, 1992 (abandoned).

FIELD OF THE INVENTION

The invention relates to a composition of active pharmaceutical agent for administration into the vaginal canal to prevent the spread and transmission of Sexually Transmitted Diseases. The present invention also relates to a composition for administration into the vaginal canal to prevent the transmission of HIV, and the spread of AIDS.

The invention also relates to a method of administration of an active pharmaceutical agent via the vaginal cavity and to a sponge capable of delivering such agent into the vaginal canal during insertion of the sponge, while the sponge is resident in the vagina and during removal from the vagina.

The present invention also relates to vaginal sponges for the topical or systemic, sustained release of a wide range of active pharmaceutical compounds. And the invention relates to sterile, packaged vaginal sponges containing predetermined dosages of active pharmaceuticals which sponges can be conveniently inserted and removed by the user without compromising the predetermined dosage and without waste or mess.

THE PRIOR ART

Sexually Transmitted Diseases

The term "Sexually Transmitted Disease" (STD) is a relatively new one that has gradually replaced the term "Venereal Disease." This terminology has expanded not only the awareness of infectious diseases transmitted through sexual contact, but now describes an expanded array of diseases.

Venereal diseases originally encompassed five traditional infections: Gonorrhea, Syphilis, Chancroid, Lymphogranuloma Venereum, and Granuloma Inguinale. The term STD today includes more than twenty specific organisms and syndromes, including HIV, Chlamydia Trachomatis, Genital Herpes, Genital Warts and Cervical Neoplasia. Thus, the use of the term STD has grown in its scope, and now encompasses a large number of sexually transmitted infections. These include Acquired Immunodeficiency Syndrome (AIDS), Acute Urethral Syndrome or Cystitis, Bacterial Vaginosis Vulvovaginitis, Candidiasis, Cervical Intraepithelial Neoplasia, Chancroid, Chlamydia, Cytomegalovirus infections, Enteric infections, Genital Warts, Gonorrhea, Granuloma Inguinale, Hepatitis B, Herpes Genitalis, Human Papillomavirus (HPV), Lymphogranuloma venereum (LGV), Molluscum Contagiosum, Mucopurulent Cervicitis, Nongonococcal Urethritis, Pediculosis Pubis, Pelvic Inflammatory Disease (PID), Scabies, Syphilis, Trichomoniasis and Vulvovaginitis.

STDs are getting worse both in magnitude and severity. A large and growing number of pathogens have been implicated as causative agents. To name a few of the causative agents currently known, Acquired Immunodeficiency Syndrome is caused by Human Immunodeficiency Virus (HIV). Acute Urethral Syndrome is caused by *E. coli*, C. trachomatis, N. gonorrhea and other gram-negative bacteria. Cervical Intraepithelial Neoplasia (CIN) has been associated with human papilloma virus (HPV), and the Herpes Simplex Virus. Chancroid is caused by Hemophilus Ducreyi. Chlamydia, one of the most common bacterial STD infections in the United States, is caused by Chlamydia trachomatis. Cytomegalovirus infections are caused by a DNA virus of the Herpes virus group. Enteric infections, which are outside, but are related to STDs, are caused by many sexually transmissible bacteria, viruses and protozoa, and by other organisms that produce disease, and are carried in the gastrointestinal tract. Genital Warts are caused by the human papillomavirus (HPV), a small DNA virus belong to the papillomavirus group. Gonorrhea is caused by Neisseria Gonorrhea, a gram-negative diplococcus. Granuloma Inguinale is caused by the gram-negative bacteria calymmatobacterium granulomatis. Hepatitis B is caused by Hepatatis B virus (HBV), a DNA virus with multiple antigenic components. Herpes Genitalis is caused by the Herpes Simplex II virus (HSV). Lymphogranuloma venereum (LGV) is caused by immuno-types L I, L II, or L III of Chlamydia Trachomatis. Molluscum Contagiosum is caused by the Molluscum Contagiosum virus, the largest DNA virus of the poxvirus group. Mucopurulent Cervicitis is caused by Chlamydia and Gonorrhea. Nongonococcal Urethritis (NGU) is caused by Chlamydia of the D to K immunotypes. Pediculosis Pubis, which, strictly speaking is not a true sexually transmitted disease, is caused by a pubic or crab louse, an ectoparasite. Pelvic Inflammatory Disease (PID) is caused by Gonorrhea, Chlamydia, and other anaerobic bacteria and gram-negative rods, such as *E. coli* and mycoplasma homines. Scabies is caused by Sarcoptes scabies, a female mite approximately 0.4 mm long. (Although not a true STD disease it is commonly found among those with other STD infections). Syphilis is caused by Treponema Pallidum, a spirochete. Vulvovaginitis is caused by Trichomonas Vaginalis.

As can be seen from the foregoing, a broad variety of microorganisms can potentially enter the vaginal tract through sexual intercourse, and result in a sexually transmitted disease. These microorganisms include bacteria, viruses, fungi, protozoa, and yeasts among others. The health consequences which can result from the contraction of a sexually transmitted disease can be severe, and extremely debilitating. The risk of contracting AIDS through sexual intercourse, for example, is a major concern for many individuals.

From a health care perspective, numerous other sexually transmitted diseases, as provided, for example, in the listing above, are likewise a potential concern. Accordingly, there is a need in the prior art for a chemical composition or medication for administration into the vaginal canal to prevent the tranmission and spread of sexually transmitted diseases, including AIDS.

Thus, there is need for suitable and effective microbiocides which would kill microorganisms in the vaginal canal before they can cause infection. In addition, there is also a need for effective contraceptive agents and preparations for use before or during sexual intercourse, as well.

The Vaginal Sponge

One of the primary concerns encountered when medication is to be administered to an individual is that the medication reach the targeted area of treatment and be maintained in that targeted area. For example, when treating vaginal disorders it is often desirable that medication be applied for extended period of time to remote regions of the vaginal canal or cervix. These regions are not readily accessible by conventional vaginal suppositories due to their size and shape. Moreover, because of the structure and nature of the vaginal canal, inserted suppositories often do not stay in place or, upon melting, may drain out of the vagina substantially reducing the effectiveness of the medication. Vaginal foams formed by delivering foam-forming materials into the vagina are short lived and hence are unsuitable for sustained release of active agents. Moreover, both vaginal suppositories and vaginal foams are very messy to use. Use of tampons and other similar devices have not proved successful because of their configuration and the nature of their compositions.

Physical swabbing and douching can cleanse the vaginal canal, but neither can provide sustained release of active agents.

Contraceptive vaginal foam sponges have been previously proposed but even those currently in commercial use do not provide for a predetermined level of sustained release of spermicide and medicaments over a given period of time.

Clinical studies have indicated that young women using oral contraceptives may increase their risk of developing breast and cervical cancers in midlife. Whether this type of contraception is dangerous is debateable but it is recognized that the "pill" interferes with the hormonal balance of the user. Multiple and considerable side effects from the use of oral contraceptives have been observed in many women.

Many attempts to find safer and more effective contraceptive methods which reduce or eliminate side effects have been made. A 24-hour vaginal contraceptive sponge has been commercially marketed. The device comprises a polyurethane sponge disc having a central recess and containing 1,000 milligrams of a spermicide known as nonoxynol-9, which is generically known as nonylphenoxypoly (ethyleneoxy)-ethanol.

While the contraceptive sponge has met with some success in the market place, its usage has been accompanied by drawbacks. Use of the device requires that the spermicide be activated by adding tap water to the sponge and requires manual manipulation of the sponge. Such procedures present numerous disadvantages:

(a) It is virtually impossible to accurately measure the volume of water coming out of a standard faucet, therefore the spermicide is often diluted to less than an effective amount or is insufficiently diluted. Application of the uniform effective amount of active spermicide is unpredictable because it depends on the amount of water run through the sponge.

(b) The tap water may contain contaminants, including bacteria that destroy of impair the sterility of the contraceptive sponge.

(c) The water may contain contaminant chemicals, such as chlorine and fluorides, that may interfere and react with the therapeutic agents contained in the contraceptive sponge.

(d) The contraceptive sponge cannot be immediately inserted or used after removal from its package, i.e., the sponge does not contain active spermicide but requires activation with water.

U.S. Pat. No. 5,070,899 ('899 patent) describes bactericidal, viricidal polyurethane sponges containing iodine or chlorhexidine and a spermicide surfactant. It is used as a contraceptive. The purpose of the iodine is to provide protection against toxic shock syndrome. The patent does not discuss how the active ingredients are released nor does it attempt to address the medical or contraceptive applications for which it is allegedly used.

U.S. Pat. No. 4,393,871 ('871 patent) relates to the administration of medicaments. The medicament or spermicide enters the '871 product in the solution which makes the foam sponge. Thus when the resulting device is molded, cured and dried, the medicament is incorporated therein and must be reactivated into a foam by the use of tap water before application. There is no hermetically sealed sterile package to prevent intrusion of foreign organisms.

The '871 sponge is said to be reusable like a diaphragm for many repeated applications and thus is not sterile after its first use. The release of foam carrying the active ingredient is problematic because the foam must be agitated to create the foam.

There is no water release of activated spermicide because the water level used to create the foam is blocked in the foam structure.

The amount of water originally added to the '871 system is not controlled or consistent and is only sufficient to generate initial foaming. The cells of the foam cannot be saturated, or partially saturated with liquid to provide liquid release during use because to do so will cause complete disintegration of the sponge in the vaginal cavity.

An alternative sponge-type contraceptive, packaged in a hermetically sealed, air tight foil packet has also been proposed in Gero, U.S. Pat. Nos. 4,693,705 ("'705 patent") and 4,692,143 ("'143 patent"). The spermicide is preactivated and carried in a solvent of distilled water impregnated into the sponge so that the sponge can be used upon removal from its packet. The contraceptive contains no more than approximately 1650 milligrams of solution per sponge and does not release the spermicide in the vaginal canal. The sponge is merely a blocking device and does not provide for sustained release of the activated solution.

The '705 and '143 patents teach that a solution is injected in the foam. The solution is, however, totally "blocked" because the size and construction of the sponge and the amount of solution introduced therein are such that no release of fluid from the sponge is possible. Solution release is not described nor is sustained release described for prolonged medicinal action.

Long Felt Need in the Art

There is currently a need in the art for a broad spectrum microbiocide for administration into the vaginal canal to prevent the transmission and spread of microorganisms which can cause a sexually transmitted disease. There is also a particular need in the art for a microbiocide effective in preventing the transmission of HIV, and thereby, reducing the spread of Acquired Immune Deficiency Syndrome (AIDS).

There is also a need in the art for a vaginal device that can deliver an active agent, such as medication, to areas within the vagina and/or into the bloodstream via the tissue of the vaginal canal and be maintained within the vagina for a prolonged period of time. There is a further need for a removable vaginal device which releases a spermicide or other active agent throughout the vaginal canal while being inserted and removed and which will release from the device a spermicide or other active agent for a prolonged period of time upon normal body movements of the wearer.

Objects of the Invention

It is an object of the present invention to provide a chemical composition which acts as a microbiocide to kill a broad spectrum of microorganisms which can become introduced into the vaginal canal during sexual intercourse.

It is a further object of the present invention to provide a chemical composition which is effective in preventing the spread and transmission of the HIV virus during sexual intercourse.

It is a further object of the present invention to provide a chemical composition which reduces the spread of sexually transmitted diseases.

It is a further object of this invention to provide a vaginal sponge that can deliver an active pharmaceutical agent, topically or provide for its absorption into the systemic bloodstream via the vaginal canal.

It is a further or related object of this invention to provide a vaginal sponge that can deliver such active pharmaceutical agents over an extended period of time through a sustained release action.

It is a related and further object of this invention to provide a vaginal sponge which when inserted and when removed releases a prescribed dosage of active pharmaceutical agent in a suitable carrier for swabbing the walls of the vaginal canal.

It is a further related object of this invention to provide a vaginal sponge which can be inserted and removed by the user without professional assistance and which can be done so without mess, waste, creation of unsterile conditions or compromise of the dosage of active pharmaceutical agent contained in the sponge.

It is a further related object of the invention to provide a vaginal sponge which blocks and encapsulates the cervical os while releasing a prescribed dosage of active pharmaceutical agent over an extended period of time.

It is still a further and related object of this invention to provide sponges having a range of cell sizes and configurations such that they are optimized for the containment and release of a range of active pharmaceutical agents of different molecular configuration and molecular weight contained in a range of carrier vehicles.

SUMMARY OF THE INVENTION

These objects of the present invention are achieved by providing various chemical compositions for introduction into the vaginal canal, and a chemical delivery system for delivery of the chemical agents into the canal, as described herein.

A variety of chemical compositions are disclosed which act as a highly effective microbiocide. The preferred chemical composition for microbiocidal action comprises a mixture of Nonoxynol-9, Benzalkonium Chloride, and Povidone Iodine. This composition is valuable both as a broad spectrum microbiocide, useful in killing a broad spectrum of harmful microorganisms, and as a preparation useful in killing the HIV virus.

As an alternative to the above, a combination of Nonoxynol-9 and Povidone Iodine in which Benzethonium Chloride is substituted for Benzalkonium Chloride may also be used.

Numerous other chemical compositions are disclosed in this application as well. They include microbiocide preparations, chemical compositions for contraceptive use, and compositions effective for a variety of differing disorders.

For example, a novel spermicide, Benzethonium Chloride, is disclosed as well. Benzethonium Chloride may also be used on its own as a spermicide, or microbiocide. Alternatively, it can be used in conjunction with Benzalkonium Chloride, which is already well known in the art. The present chemical composition can be directly applied to the vaginal canal, or incorporated in a device for insertion into the vaginal canal, such as a vaginal sponge, or in another appropriate vaginal device.

In the preferred embodiment for a delivery system for the chemical composition, these objects of the invention are also achieved in a product designed for delivery of chemical agents into the vaginal canal. The product comprises a sponge impregnated with the liquid containing an effective amount of the active pharmaceutical agents, the liquid being present in an amount greater than that which is blocked within said sponge, but less than the saturation value of the sponge so that when the sponge is implanted in the vaginal canal it will release liquid therefrom. The sponge is preferably provided in a sealed, air-tight package. Thus, the present invention now provides a removable, premoistened vaginal sponge impregnated with a solution containing a carrier and an active pharmaceutical agent. The sponge contains both an amount of solution that is tightly held by the sponge, i.e. blocked therein, and a freely releasable amount of solution that is released upon mechanical deflection, i.e. squeezing of the sponge.

In addition, a method is disclosed in the application for voluntarily releasing chemical agents into the vaginal canal, from the sponge, at will, while the sponge is seated within the vaginal canal. The method involves the use of Kegel's exercises to compress a vaginal sponge to release chemical agent from the sponge at will.

As used in the specification and claims of this application, the term "microbiocide" refers to chemical compounds and agents effective in destroying microorganisms. The terms "releasable" or "freely releasable" or "mechanically releasable" are used interchangeably and mean an amount of liquid that can be expelled from the sponge by simple compression or squeezing of the sponge. The term "tightly bound" or "blocked" means an amount of liquid retained by the sponge even when compressed and which is only removable from the sponge by some type of non-mechanical means, such as evaporation. The term "saturation value" means the maximum amount of liquid that can be held by the sponge. A saturated sponge will release liquid immediately upon being squeezed.

According to one embodiment of the invention there is provided a vaginal device comprising a hermetically sealed air tight package enclosing therein a sponge impregnated with a liquid containing an active pharmaceutical agent, the amount of liquid being sufficient to provide a reservoir of the liquid while the sponge is in place in the vagina. The sponge contains a mechanically releasable amount of liquid containing an active pharmaceutical agent and that releasable amount of liquid may contain or itself may comprise a prescribed unit dosage for a specific window of therapy or half-life drug metabolism.

According to another embodiment of the present invention, there is provided a vaginal device comprising a hermetically sealed, air tight package enclosing therein a sponge impregnated with an amount of liquid containing an active agent, such that when the sponge is implanted in the vaginal canal, prescribed body movements of the wearer will cause the sponge to be squeezed to thereby provide release of liquid from the sponge.

The invention is also in a sponge that is easy to insert and remove. It is a vaginal for administration of both systemic and topical drugs. It can provide for topical protection from sexually transmitted microorganisms, provide a method for removing vaginal debris and can also be used to provide non-systemic contraceptive birth control.

How the Vaginal Sponge Invention Works

The freely releasable or excess amount of the solution acts as a reservoir of the active agent. Liquid is released from the sponge as it is inserted into the vagina and the released solution coats the vaginal tissue. Similarly, the sponge releases additional liquid from the reservoir as it is removed from the vaginal cavity. When the sponge is in place, additional amounts of liquid are released over time from the reservoirs as the sponge is compressed or squeezed by prescribed body movements, at prescribed time intervals.

The "freely releasable" portion of the solution is released upon the simple squeezing of the sponge. When the sponge is inserted into the vagina it provides its own lubricating action. It gently expands the entire vaginal tissue and applies a film of solution which fully coats the vaginal tissue for both topical or systemic active pharmaceutical compound absorption.

Upon reaching its seating position in the vagina, the sponge containing the predetermined liquid reservoir of carrier and active agent may then release liquid by the gentle mechanical pressure created by intercourse or by certain muscle groups and tissue generated by what is known as "Kegels exercises" or by similar naturally occurring bodily movement. The released quantities of solution are distributed throughout the entire vaginal cavity by simple diffusion. Such release provides a "well" of formulated solution at the point of the external os of the cervix wherein capillary action then draws the solution into the cervical cavity.

During this process of releasing active agents, the sponge device is in position to block the entire vaginal fornix. The released solution provides a liquid gasket surrounding the entire device. The device accommodates the protruding cervix providing for additional blocking action of the external os.

The sponge of the invention may be used for sustained release of a liquid containing a carrier and an active agent for a prolonged period of time to a targeted site within the vagina. The active agent may be a medicament. Alternatively, the sponge may contain a carrier containing a spermicide that is released from the reservoir to the vagina, thereby acting as a contraceptive. Upon bodily movements of the wearer that squeeze the sponge the "freely releasable" amount of the liquid containing the spermicide or other active agent etc. is released from the reservoir. Some liquid will travel into the cervix. Some liquid will travel down the vaginal canal. Some liquid will form a film covering the sponge. The sponge may be maintained within the vagina for prolonged periods of time while continuing to provide release of the active agent from the reservoir.

Use of the Vaginal Sponge Invention as a Contraceptive

Attempts to find safer, and more effective contraceptive methods have long been sought. The sponge of the invention provides a 24-hour period of vaginal conception protection by releasing not only an active spermicide, but also by blocking the entire vaginal fornix cavity, thereby encompassing the external os and providing a wall to prevent the transmission of sexually transmitted diseases, as well as by blocking the cervical cavity to prevent intrusion thereinto. The configuration of the sponge accommodates the female anatomy by embedding the external os into its soft foam construction. Such configuration ensures that a fountain or well of medicated solution is absorbed by capillary action well into the cervical canal.

The sponge of the invention provides for the subsequent absorption and removal of debris after a sexual occurrence. It coats the entire vaginal tissue with a microbiological killing formula during removal, providing for additional protection from sexually transmitted organisms. By its ability to release active formula over a 24-hour period, the sponge of the invention accommodates anticipated as well as multiple sexual episodes. Thus, each time the wearer anticipates coitus, she will cause the implanted sponge to be squeezed by Kegels exercises or other similar naturally occurring bodily movements, to release an effective amount of spermicide.

The sponge is completely disposable. It offers the substantial advantage of having no side effects common to oral contraceptives. Its predetermined and controlled level of active ingredients have no side effects common to other barrier or medicament contraceptives, including allergic reactions, lesions, and pain. No additional water or activators are necessary for use. The invention is available for immediate use from its sterile air tight package.

When used as a contraceptive the sponge containing a solution of a spermicide immobilizes sperm five ways:

(a) By completely swabbing the entire vaginal wall upon insertion;

(b) By providing a liquid gasket to prevent sperm from bypassing the fornix cavity;

(c) By release of freely releasable liquid which bathes vaginal tissue during the period of use;

(d) By providing a blocking action by maintaining a "tightly bound" residue within the device; and (e) Upon removal of the device, by releasing a more active agent.

Use of the Vaginal Sponge Invention for Delivery of other Active Pharmaceutical Agents Systemic drug products have historically been formulated for administration to the body by oral, buccal, sublingual, rectal, parental, topical, and inhalation routes. The invention provides for vaginal absorption of systemic drugs.

The prerequisite for absorption of any drug through the human skin, and vaginal tissue is of the same characteristic as the human skin, is that the drug be dissolved in an appropriate solvent. Drugs taken orally or by other methods other than direct introduction into the blood stream, undergo enzymatic destruction in the body. A substantial portion of the drug may be rendered inactive by various metabolic processes. Substantial excesses of the drug thus must be added to the "window of therapy" to compensate for this destruction. The result can be to cause side effects characteristic of the drug.

In the process of absorption through the skin, all drugs must penetrate several semi-permeable cell membranes before reaching the blood stream. In the case of skin absorption, the stratum corneum of the skin tissue represents the controlling phase between the entry of the drug at the skin surface and its passage into the lower layers of the skin which distribute the drug into the blood stream.

The lower the molecular weight of the compound being administered, the higher the rate of diffusion. With the use of penetration enhancers delivery of the molecules is enhanced, diffusion is accelerated and penetration through the vaginal membrane is accomplished. The invention contemplates the use of drugs in an appropriate carrier at high concentrations. The drug will be released on a sustained basis over a relatively long period of time without the need of extensive and expensive clinical visitations. The device is one that can be self-administered with relative ease.

Because all applications for this form of drug delivery require water as the preferred solvent, a properly designed polyurethane foam structure is preferred to achieve the administration of systemic drugs. Such structures are also preferred for administration of topical medicaments for specific local vaginal conditions.

For the correction of soft tissue pelvic infections, the antibiotics of choice are quickly destroyed, and poorly absorbed. Oral penicillin requires higher dose levels to cover gram/negative anaerobes. Cephalosporines (because oral agents are not equivalent) must be delivered by other than oral administration. The invention achieves the delivery of the required antibiotics and other medicaments through the vaginal cavity, provides the advantage of self-administration, and, more importantly, assures effective dose levels in the blood stream.

For example, the sponge of the invention may be used for:
(a) estrogen replacement therapy, by sustained release from the sponge of estrogen;
(b) vaginal pH control, by sustained release of acidic agents;
(c) vaginal cleansing, by coating the vaginal wall during insertion of the sponge with suitable agents and removal of debris from the vagina during removal of the sponge from the vagina;
(d) treatment of viral infections, such as genital herpes, by sustained release of an antiviral agent, such as acyclovir;
(e) treatment of N. gonorrhea, by sustained release of a suitable agent, such as tetracycline;
(i) treatment of vaginal yeast infections, by sustained release of a suitable agent, such as Metronidazole;
(g) treatment of vaginal infections, such as cervicitis and endometritis, by sustained release of tetracycline or other broad spectrum antibiotics;
h) cure of neisseria gonorrhea by administering a tetracycline at materially lower dose rates per systemic application;
i) cure of chlamydia and candida albicans vaginitis using an appropriate sustained release violet dye solution;
j) cure of trichomonas vaginalis vaginitis using a sustained release metronidazole solution; and
k) relief of vaginal itch caused by non-specific yeast infections by administering an appropriate medication designed for overnight application.

In topically medicating the vaginal cavity, the primal concern is that the prescribed dosage reach the targeted area for treatment and that the medicament remains in place for the prescribed period of time at effective dose strength. Other methods of administering active pharmaceuticals, including the use of suppositories, foams, gels, or even mechanical swabbing do not achieve these desired objectives. None of these other methods provides for the cleansing of blood, mucus, cells, and other destructive debris. The ability to provide for sustained release from a sponge which remains in the desired therapeutic position assures target penetration and complete cleansing of the tissue.

Suitable active agents can be delivered by the sponges of the invention, including without limitation:
(a) Anti-infectives, such as antibiotics, including penicillin, tetracycline, chlortetracycline, bacterin nystatin, streptomycin, neomycin, polymyxin (sulfate salt form), gramicidin, oxytetracycline, chloramphenicol and erythromycin; sulfonamides, including sulfamethizole, and sulfisoxazole; antivirals, including idouridine; and other topical antibacterials, including nitrofurazone, providoneidine, and sodium propionate; magnesium gluconate; benzalkonium chloride; benzethonium chloride;
(b) Anti-inflammatories such as hydrocortisone, cortisone, dexamethasone, fluocinolone acetonife, triamcinolone, and various prednisolone acetonide; triamcinolone, and various prednisolone compounds;
(c) Estrogenic steroids such as estrone, 17 N-estradiol ethanol estradiol and diethylstilbestrol;
(d) Progestational agents such as progesterone, 19-norprogesterone, norethynodrel, and 17-hydroxyprogesterone; and
(e) Prostaglandius such as PGE 1, PGE 2, PGF1, PGF2a, and the like.

The active agents can be in a variety of forms, such as uncharged molecules, components of molecular complexes, or nonirritating, pharmacologically acceptable salts such as hydrochloride, hydrobromide, sulfate, phosphate, nitrate, borate, acetate, maleate, tartrate, salicylate and the like. For acidic drugs (e.g. quaternary ammonium) can be used. Additionally, simple derivatives of the active agent such as ethers, ester, amides and the like which have desirable retention and release characteristics but which are easily hydrolyzed by body pH, enzymes, etc. can be used.

The amount of active agent incorporated in the vaginal device of the present invention varies, depending on the particular active agent, and the desired therapeutic or prophylactic therapy. The upper limit and the lower limit will depend on the activity of the active agent and the time span of its release from the device. Thus, it is not practical to define a range for the therapeutically effective amount of active agent to be incorporated in or released by the specific vaginal device administrating the medicament.

In connection with the present invention, "active agent" or "chemical composition" includes without limitation, "drug", "medication", "medicament", "spermicide" and other physiologically or pharmacologically active substances for producing a localized or systemic effect upon human tissue or effects in animals, especially mammals.

The above agents and other active ingredients can be present alone or in combination with pharmaceutical carriers to make the active agents more easily absorbed through the surface of the vaginal tissue. The device may also contain adjuvants for preserving, stabilizing, wetting, emulsifying and the like. Such compounds have also been used in combination as antibiotics, anti-yeast, or anti-fungal agents, as well as agents to destroy sexually transmitted diseases.

The Physical Nature of the Sponge

The sponge is a specifically configured polyurethane foam structure having characteristics specific for the administration of selected medicinal agents. Generally it is known that (a) the larger the cells of the sponge, the more liquid the sponge will contain (per cubic measure) and conversely, the smaller the cells, the less liquid it will contain (per cubic measure), (b) the amount of liquid absorbed within a sponge varies in relation to the viscosity of the liquid being absorbed and is also affected by the design of the sponge skeleton, (c) the construction of the component cells forming the foam skeleton, although equal in their number per lineal inch of sponge, determines its absorbent capacity, and (d) the density of the sponge, the compression deflection (pressure required to move the sponge in various directions), the water wicking and the tensile strength of the material used are all important factors in determining the characteristics of a given sponge for its assigned use and all bear upon the retention and release of the liquid contained therein.

Polyurethane polymers are a family of foamable hydrophilic polyurethane prepolymers derived from toluene diisocyanate. They react with protic compounds to form elastomeric foams. The shape of the resulting foam skeleton structure, the size and shape of the individual cells forming the structure, the size and shape of the resulting foam skeleton structure, the size and shape of the individual cells forming the structure, and the number of cells in a given structure are all determined by choice of and amount of surfactant additives suspended in the aqueous solutions from which the foams are added and by the conditions of the foam-forming methods.

These variables determine the specific characteristics of absorption and release of a solution retained in the structure. Each of these variables must be custom considered to provide for the flow characteristics of the solvent to be used and the nature of the molecular structure of the compounds being administered.

Polyurethane copolymers are used because they offer medical softness. "Polyether" compounds as opposed to a "polyester" compounds are used because the primary solvent, water, will destroy polyester compounds. Most polyurethane foams have a long shelf life if protected from moisture. It is important to this invention that a "polyether" copolymer structure be used, because it allows the foam to be fully subjected to and immersed in aqueous solutions which are the carriers of the medicaments of choice.

The commercial grades of polyurethane polymers are based on toluene diisocyanate. This compound is water activated and no catalysts are required. A high level of additives can be introduced into the aqueous phase to determine the properties required for cell structure design. This provides for high foam purity by eliminating the need for catalysts and allows for a broad range of cell structure design by varying the choice and amount of surfactants.

Although the foams of the invention will be subjected to a wide variety of medicinal chemical compounds it has been found that these do not materially affect the performance of the sponge. The prepolymers used for producing the foam of the invention must be thoroughly safety tested to assure that there is no toxicity of any kind including oral, inhalation, dermal and mutagenicity.

The design of the individual cell structure and resulting skeletal structure of the foam is important to the proper operation of the tampon of the invention. The chemical reaction and the release of heat and gases in the foam-forming process is actuated by water. The process is designed to create a foam specific to the molecular characteristics of the medicament to be delivered.

A given surfactant, which creates the cell shape, is really a form to which the plastic polymers adhere. It develops the size and shape characteristics of the foam components. The resulting gases released from the chemical reaction also help form and determine the physical characteristics and shape of the individual cells that link themselves to form the spherical skeleton of the foam structure. The surfactants determine how many cells are formed in the spherical skeleton of the foam structure, the size of the individual cells, the number of them being linked and whether the individual cells are open or closed. Each of these parameters materially affects the construction and therefore the fluid dynamics of a specific foam device. The solution flow dynamics, or how fast or how slow a solvent will be absorbed and/or released from the sponge, is a major factor in the design of the sponge.

Foam flexibility and texture are controlled by varying the amount of water and additives. In some instances catalysts are used to generate heat to produce certain configurations; however, the residues of both catalysts and additives have a significant effect upon the toxicity and the biocompatibility of the resulting foam structure with skin tissue and in particular with vaginal tissue.

PREFERRED EMBODIMENTS

In a preferred embodiment of the chemical agent delivery system invention, the sponge is a polyether derived polyurethane foam sponge. In another preferred embodiment of the invention, the polyether polyol derived polyurethane foam preferably has from about 50 to about 250, most preferably about 50 to about 200, cells per lineal inch, such cells preferably being fully reticulated. The density of the polyurethane foam sponge is preferably at least about two pounds or more per cubic foot, and the tensile strength is preferably at least about 15 to about 30 psi. Because of this very strong tensile strength, there can be no chance that pressure on the sponge during insertion or removal of the sponge, or tearing by a fingernail will cause a portion of the sponge to break off and become a foreign object in the vaginal cavity. Desirably, the sponge is able to absorb at least about 10 times its weight of water and preferably about 15 to about 25 times its weight.

The cells of the polyurethane foam structures used in the invention resemble spheres with open spaces allowing for the free flow of air or solution. They are not, as commonly thought, inflated balloons. It is important that the cell structure include linking cells. It is also important that the cells initially look like an elongated "donut" with a membrane across the hole, but that the membrane of each cell be destroyed mechanically and the scrap membrane removed from the resulting open foam structure. No dust or other physical particle should be released upon solution entry. The gas explosion reticulation method of production is of particular importance, not only to remove potential chemical scrap, but to allow the full opening of the "donut hole" to provide a quicker and freer movement of solution.

The preferred polyurethane cell structures take the shape of an oval window having in its center a membrane which is subsequently reticulated to remove said membrane and all dust or other particles of production. Depending upon the surfactant used in production, and the copolymer selection, various sizes of polyurethane cells will result. Such reticulated chain of cells will combine to produce a series of spherical shapes which construct the foam skeleton. Such combination of cells will vary from a low of 10 cells to a high of 15 cells per developing sphere. The preferred spherical structure is 12 reticulated cells, and is determined by the selection of chemical components and equipment used in creating the polyurethane foam.

The resulting spherical structures will determine the size of the solution particles that will be incorporated into each spherical structure. When used as a contraceptive, the foam has about 100 cells per lineal inch. The preferred construction may have between 50 cells to 250 cells per lineal inch depending upon the volume of the sustained release reservoir required, the viscosity of the solution and the required drug blood levels to be attained to achieve an effective dose. Such structures to assure the proper density and tensile strength of the foam.

The design of the sponge preferably follows the contour of the vaginal cavity. This allows the sponge to naturally orient itself to its seating position. The sponge is preferably designed to easily proceed and glide under the cervix to the posterior wall of the vagina. Preferably, the sponge is a sphere with opposed and most preferably parallel flattened top and bottom portions. Most preferably, the sponge is symmetrical about a plane passing through and parallel to the top and bottom portions. The flat surfaces and the curved body portion of the sponge accommodate the vast variety of differences in the dimensions of the female anatomy. A vast variety of sizes, shapes, and position of tissue in the vaginal anatomy are encountered, and each is accommodated by the sponge of the invention.

It is believed that the sponge of the invention works by having a great complex of connected cell structures which form spheres. It is not the individual cells that hold the liquid, but the resulting spherical configurations. There may be approximately one million cells in a cubic inch of foam sponge material. When the sponge is immersed in a liquid and the trapped air is removed, the liquid enters and fills the resulting spheres. Because these spheres are so small, the "cohesive" forces created by air pressure upon the liquid, force the liquid into the spheres where it forms droplets the size of the resulting spheres.

The droplets are held in place by "cohesive" pressure. The liquid remains in this position in the spheres until there is another form of pressure applied to counter the "cohesive" pressure. Physical squeezing, or the release of the "cohesive" pressure by the heat of evaporation or other pressure must be applied. If there is no mechanical pressure or evaporation, liquid will remain in the sponge indefinitely when it is placed in a sealed, air-tight package.

When compression is applied to the sponge, the cells release the freely-releasable droplets from the spheres because the squeezing pressure applied is stronger than the "cohesion" pressure. The cell walls are still wet and the liquid clings by "adhesion" created by "surface tension". The "tightly bound" liquid sticks to the cell structure. This tightly bound liquid cannot be removed by mechanical squeezing because the "adhesion" surface tension is stronger than the squeezing pressure that can be applied.

In accordance with the invention, the foam sponge is formed and then impregnated with the desired solution of active agent. This means that the surfactant required to form the polymer foam can be selected without regard to its use as a releasable active agent. Hence the surfactant can be selected to affect the dynamics of fluid retention and release for a given specified carrier. The release of liquid can be optimized by controlling the size of the polymer cells produced, which in turn is controlled by the choice of surfactant.

Different sizes and character of polymer cells are produced by different surfactants. They affect the characteristics of the resulting cells, i.e. their shape, size, size of window membrane, softness, resiliency, and tensile strength. The resulting polyurethane cells and the spherical shapes created within it determine the foam's ability to be a sustained release vehicle.

A wide variety of surfactants can be used. Nonionic surfactants work well with most polyurethane formulations. One to three percent by weight in an aqueous solution is generally effective. Other process variables such as blowing agents, the effects of pH, the use of molds and releasing agents, and other factors affect the cellular structure, density, strength, porosity, and the degree of hydrophilicity of the foam structure.

It is preferred to use a non-ionic surfactant, such as Pluronic F-68, Pluronic L-62, Pluronic P-65, Pluronic P-85, Pluronic F-127 and Pluronic F-88 as a surfactant in the manufacture of a polyether-polyol derived polyurethane foam to achieve uniform desired cell structure, density, tensile strength, porosity and the degree of hydrophilicity.

The specification of surfactant also determines the capability of the cell to be reticulated, preferably by gas explosion, thereby to provide for removal of all cell membranes and produce a fully reticulated open celled structure.

The preferred embodiments of the invention include a polyurethane foam sponge which has from 50 to 200 cells per linear inch. The sponges have a minimum density of 2 lbs. per cubic foot and can have densities as high as 4 lbs. per cubic foot and they have a minimum tensile strength of 20 psi and preferably a tensile strength of 25 psi or higher. The preferred sponges of the invention likewise have a minimum tear strength of 3 lb/inch and desirably a minimum tear strength of 4 lb/inch or higher.

The preferred sponges of the invention are impregnated with a liquid containing an effective amount of an active pharmaceutical agent, the liquid being present in broadly an amount at least greater than that which is blocked within the sponge and hence is not releasable, but less than the saturation value of the sponge. Satisfactory results are obtained where the amount of freely releasable liquid is from 5% by weight to 50% by weight of the total weight absorbable by the sponge (saturation value) and best results are obtained where the amount of freely releasable liquid is from 5% to 33% by weight. By controlling the loading of the sponge within these ranges, sufficient liquid is available to be freely releasable from the sponge upon insertion, during Kegel exercises and upon removal of the sponge but the loading is not so great as to cause dripping and loss of dosage when the user compresses the sponge after removal from the hermetically sealed package.

The Filled Sponge

One first determines the desired absorption rate of the drug compound of choice through the vaginal tissue into the blood stream and the required concentration of that drug compound in the liquid to be administered. One can then design the foam structure in which to hold the liquid containing the active agent. At that point one knows how much liquid is required, the concentration of active pharmaceutical, and the period of release.

Knowing the foregoing, one then constructs a suitable polyurethane foam, controlling cell size, skeleton size, tensile strength, density, and the size of the sponge so that it has the capacity to hold the amount of liquid desired and release the requisite amount thereof.

The amount of liquid above the "blocked level" is necessary to provide the gradient pressure to accomplish tissue penetration and absorption. The concentration of active pharmaceutical in such excess amount represents the desired concentration in the dosage to be released.

The amount of excess liquid is dependent upon the molecular weight of the active and the nature of the active, e.g. its molecular weight. The lower the molecular weight, the less liquid is required. The more compatible the molecular structure of the active with the vaginal tissue, the less active is required.

The invention achieves the release of the desired dosage into the vaginal cavity for absorption on a sustained release basis. Upon being inserted, vaginal wall tissue pressure delivers an evenly coated film all the way to the seating place of the sponge. By diffusion, the solution is distributed to the entire vaginal cavity tissue. In removing the device, the same pressures create additional release of solution to furnish a film which covers and douches the vaginal wall tissue and removes debris. Microorganisms that may have been deposited through sexual intercourse or otherwise, after introduction of the sponge, are further contacted and destroyed. Moreover, when the user applies normal muscular pressure, sometimes known as "Kegel Exercises", additional amounts of liquid are released. In certain applications, muscle contraction can and does provide a well of liquid at the external os of the cervical canal. Normal capillary action of tissue will raise the liquid into the cervical canal providing protection against microorganisms, sperm, and debris.

Packaging

It is important to maintain the concentration of active in the liquid and for the liquid within the foam to be free of mechanical pressure. Thus the foam sponge must be sealed against humidity to secure the integrity of the therapeutic dose level. Any diminution of the predetermined concentration of active or the amount of carrier may defeat the purpose of the invention. The foam must be packaged to avoid crushing and prerelease of solution by mechanical or atmospheric pressure.

BRIEF DESCRIPTION OF THE DRAWINGS

The invention is illustrated in terms of a preferred embodiment in the accompanying drawing in which.

DESCRIPTION OF A PREFERRED EMBODIMENT

Figure 1:
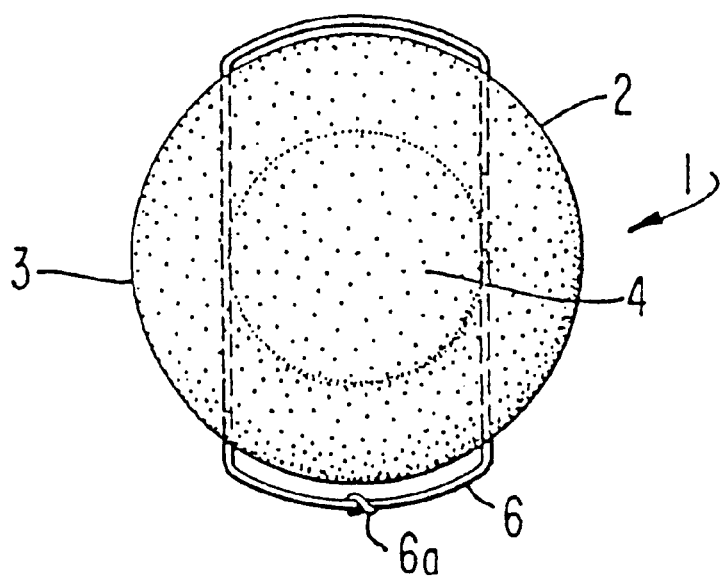
FIG. 1 is a top plan view of a vaginal sponge according to the invention.
Figure 2:
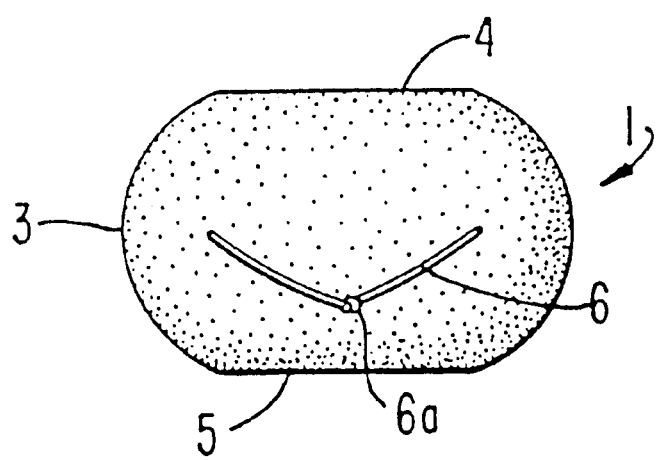
FIG. 2 is a side elevational view of the sponge of FIG. 1.
Figure 3:
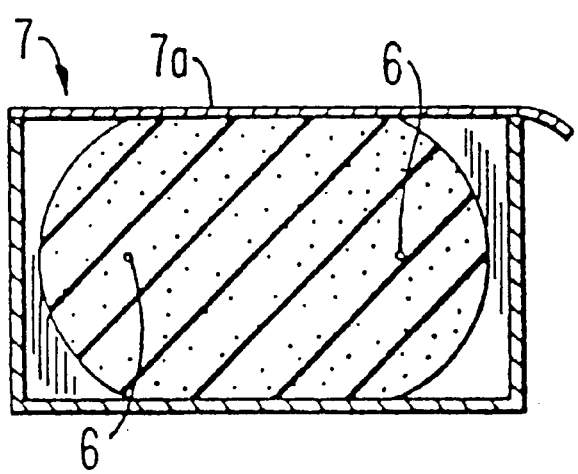
FIG. 3 is a side elevational view of the sponge of FIG. 1 in a hermetically sealed container.

Broadly, the sponge of the invention is a truncated sphere with two parallel opposed planar surfaces. Each of the planar surfaces has a diameter between 30% and 50% of the sphere diameter and preferably they are between 30% and 45% thereof. Desirably the planes are of equal size.

The advantages of such a configuration are manifold. The shape ensures that the surface of the sponge is fully curved as it enters and contacts the vagina, it provides a gliding action which follows the contours of the vaginal tissue, it conforms to the vaginal cavity, it is adjustable so that it seats in women having varied vaginal anatomies and in its seating position is sensitive to muscular pressures which cause release of the liquid contained therein.

Referring to the drawing, the sponge 1 of the invention comprises a spheroidal polyurethane foam sponge 2 having a spheroidal body 3 and opposed flattened portions 4, 5. Preferably, the sponge 2 is in the form of a sphere with parallel flats at each pole. Sponge 2 is symmetrical about a plane parallel to flats 4, 5 passing midway through body 3. Secured to body 3 in a conventional manner is a loop of string or cord 6 having a knot 6a.

Sponge 1 is contained in a hermetically sealed container 7 having a removable lid 7a. Sponge 1 contains a solution of a desired active agent and hence is hermetically sealed in container 7 to prevent loss of the solution.

Preferably the loop of string 6 extends through the body 3 and passes tightly about the rear of the body 3, with a portion depending from the front. If desired, the loop of string 6 can be substituted by a simple length of string or dispensed with entirely.

Sponge 1 may be from about 1 ¼ to about 3 inches in diameter. When used as a contraceptive sponge, a useful diameter is preferably 1 ¾ to 2 ½ inches. Suitably, the distance between the flats may be from about 1 to about 2 inches, preferably about 1 to about 1 ½ inches. Preferably, the flats 4, 5 are circles of about ¾ to 1 ¼ inch diameter, most preferably about 1 inch.

Suitably, the sponge 1 has a volume of from about 2 to about 5 cubic inches and contains from about 125,000 to about 15,600,000 open reticulated cells per cubic inch. Preferably, the sponge 1 is formed from polyether polyol derived polyurethane foam.

The sponge 1 is inserted into the vagina by being held by the fingers against the body 3, with the flats 4, 5 disposed horizontally. The sponge is lightly compressed, but under such conditions the liquid contained with the sponge is not released. Such pressure does bring solution to the outer edges of the sponge 1, which provides excellent lubrication for its entry into the vagina.

Figure 4:
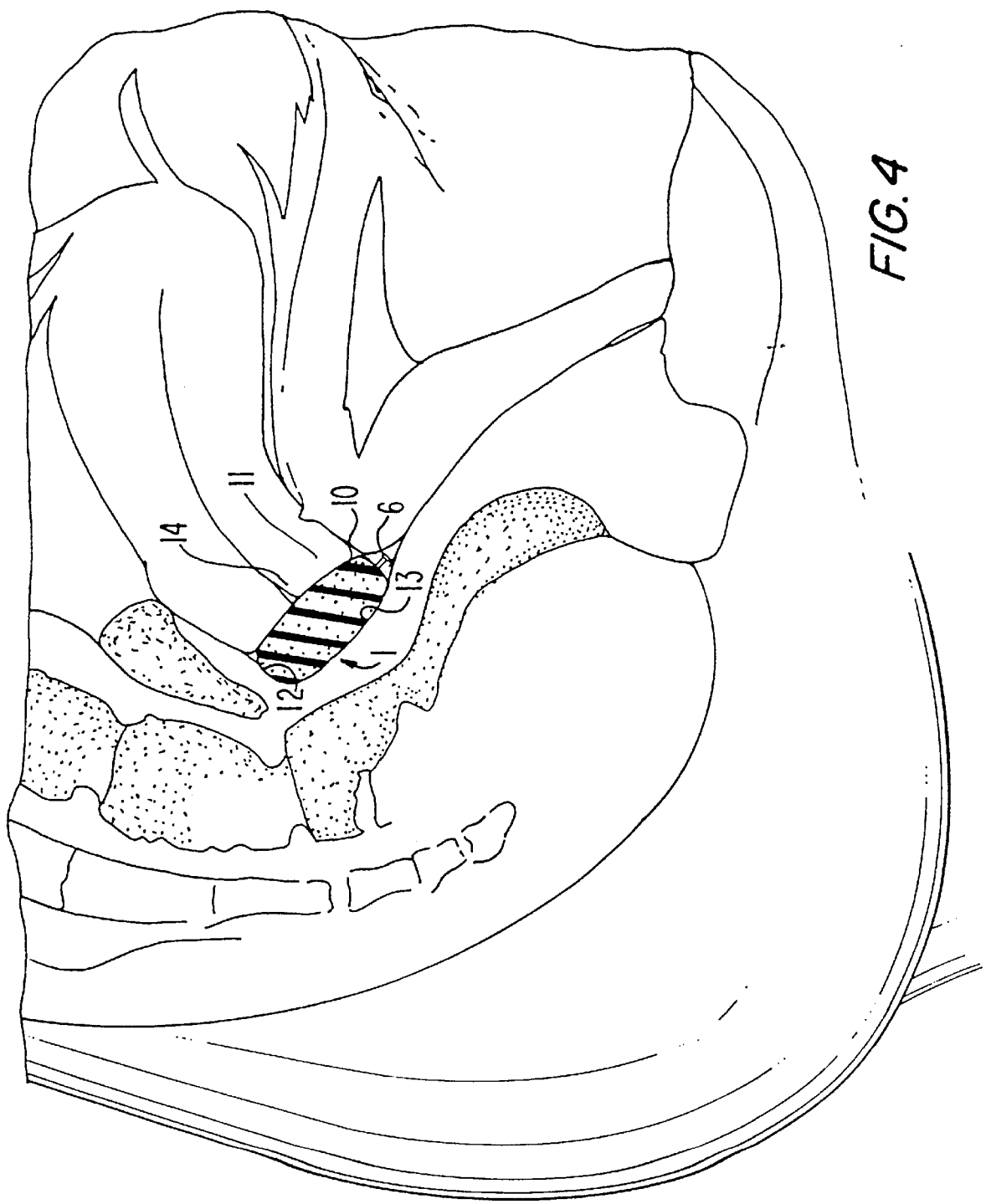
FIG. 4 is a schematic view, in section of the sponge of FIG. 1 in place in the vagina.
Figure 5:
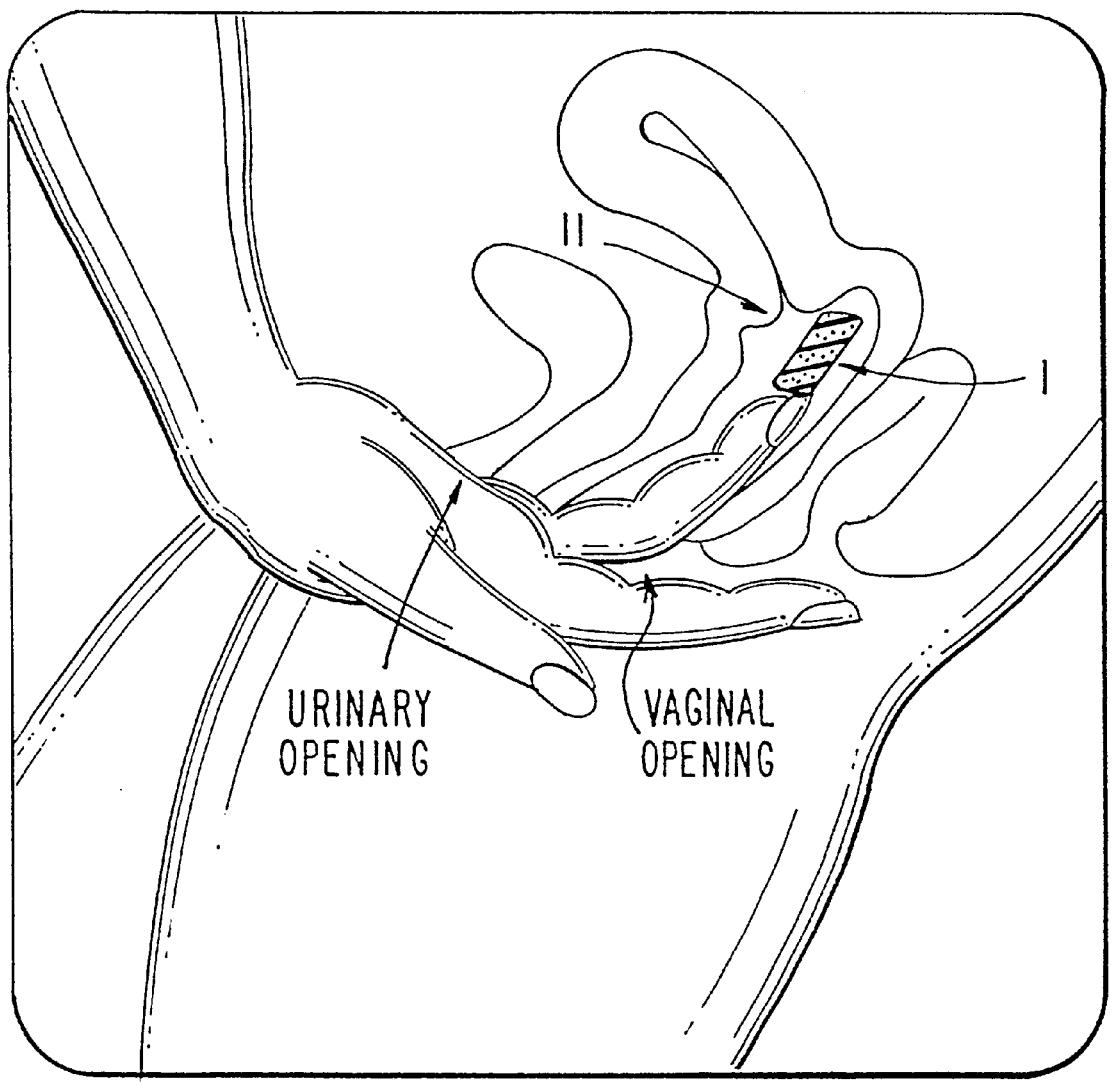
FIG. 5 is a cross-sectional view of a vaginal device, in the process of being inserted into the vaginal canal. The device will, in the preferred embodiment, contain a chemical composition therein, as described at greater length hereafter.

As the sponge 1 is directed to its seating position in the vagina shown in FIG. 4, the vaginal wall tissue is gently pushed away from its normally closed position to one following the shape of the sponge 1. The sponge 1 is thus further squeezed to release liquid so as to provide for the complete bathing of the expanded tissue surface leaving behind a liquid film of active agent throughout the entire vaginal cavity.

Upon reaching the entrance to the fornix 10, a relatively open cavity appears. The expelling pressure of the vaginal walls assisted by the lubricating action of the sponge deposits the sponge 1 into the full fornix cavity 10.

As seen in FIG. 4, the cervix 11 may be an intrusion prohibiting direct access of the sponge 1 to the full fornix cavity 10. The sponge 1 being resilient, lubricated, and designed with its curved body 3, then gently follows the fornix tissue under the cervix 11 and proceeds to the posterior wall 12 of the fornix 10. In this position, the external os 14 is completely blocked.

The sponge 1 will have been compressed in varying degrees depending upon the individual size of the user. In virtually most instances it will be compressed from its original size to an average compressed size of about ⅝ inches as measured between flats 4, 5. The sponge retains its original diameter. The compressed size of the sponge will fully accommodate the size of the individual user.

The sponge is compressible to about ¼ inch thickness. This does not occur upon insertion because the vaginal tissues of the vaginal floor 13 and the cervical cavity 3 expand. The fornix wall tissue is supple and will move to accommodate the size of the device without creating such compression to prematurely release its liquid reservoir.

The sponge 1 may be impregnated with a solution containing a stabilizing or swelling agent, such as sodium carboxymethylcellulose, which assists in creating outward pressure on the sponge to restore it to its original shape. Such pressure provides for maintenance of the sponge in its seated position during and after releasing liquid. The fit created by the tissue compression and the sponge expansion will provide for contact with all tissue. In its seating position, the sponge 1 will prevent passage and blocks sperm and semen from entering in and around the entire fornix tissue, as well as providing a double blocking action at the entrance to the fornix.

For removal of the sponge 1 from the vaginal fornix, the user may grasp the looped cord 6 and pull downward, or use her fingers to grasp the sponge 1 itself. The knot 6 a may be used as a locating adjunct to the end of the cord 6.

The method of using the sponge delivery system of the present invention may be defined as follows:

(a) removing the sponge 1 carrying the liquid containing active agent from sealed air-tight packet 7;

(b) immediately inserting the sponge into the vaginal fornix;

(c) blocking the cervix and the entrance to the fornix with the sponge and thereby providing a liquid gasket seal between the walls of the fornix and the peripheral diameter of the sponge; and (d) providing for repeated release of liquid over a period of 24 hours by applying muscular and tissue pressure upon the sponge by Kegel exercises or similar muscular pressure.

When the system is used as a contraceptive sponge, it may be inserted in anticipation of, during and after coitus for a 24 hour period, but should not be removed less than 6 hours after coitus.

As a contraceptive, the spermicide may comprise between 4 and 10 percent by volume of nonylphenoxypoly-(ethyleneoxy)-ethanol, and 0.125 to 0.250 percent of an anti-toxic shock syndrome agent. In addition, benzethonium chloride may be used in combination with the spermicide to produce a synergistic reaction for sperm immobilization. The anti-toxic shock syndrome agent is active to kill staphylococcus aureus whose toxins cause toxic shock syndrome.

The invention is further illustrated by the following examples.

EXAMPLE 1

Table 1 below provides a topical spermicide contraceptive formulation providing for sexually transmitted disease protection. The spermicide formulation is prepared by mixing the ingredients together. A polyether-polyol derived polyurethane sponge of 2 ¼ inches in diameter having about 100 cells per lineal inch and a density of about 3 pounds per cubic foot and a tensile strength of about 18–20 psi was impregnated with 6,500 milligrams of solution to provide a sponge weighing 8,200 milligrams, the dry weight of the sponge being 1,700 milligrams.

The freely releasable amount of liquid reservoir is 4,800 milligrams. In this instance, 1,000 milligrams of solution are deposited on the wall tissue to the vagina upon insertion and another 1,000 milligrams are deposited upon removal. The other 2,800 milligrams are made available for sustained release during the period of use.

TABLE 1

| Ingredient | Function of Ingredients | Composition % | Mg. |
| --- | --- | --- | --- |
| Nonylphenoxpoly-(Ethyleneoxy)-Ethanol (Nonoxynol-9) | Spermicide | 2.500 | 162.50 |
| Pectin | Vaginal Deodorant | 0.500 | 32.50 |
| Glycine | PH adjuster | 0.500 | 32.50 |
| Povidone-Iodine | Bactericide anti-TSS agent | 0.300 | 19.50 |

TABLE 1-continued

| Ingredient | Function of Ingredients | Composition % | Mg. |
| --- | --- | --- | --- |
| Sodium-Carboxymethyl-cellulose | Swelling agent | 0.160 | 10.40 |
| Benzalkonium Chloride | Bactericide, anti-fungal, anti-yeast and anti-mold agent | 0.150 | 9.75 |
| Distilled Water | Solvent | 95.890 | 6,232.85 |
| TOTAL | | 100.000% | 6,500.00 mg |

This embodiment provides a broad spectrum of protection from a variety of microorganisms. The combination of the three active ingredients Nonoxynol-9, Benzalkonium Chloride, and Povidone Iodine is a preferred combination for providing a safe, effective means of protection from sexually transmitted diseases. In addition, this chemical composition is a highly effective formulation for preventing the sexual transmission of AIDS.

With respect to the prevention of AIDS, the formulation's effectiveness rests both in destroying both free virus and virus-infected cells. Both free virus and infected cells in bodily fluids can cause the spread of HIV and AIDS through sexual intercourse. During unprotected sexual intercourse, male infected cells can and do survive in the female reproductive tract, and act as reservoirs and factories for virus production. Thus, the present formulation's effectiveness in destroying both free virus and infected cells, while also providing a broad spectrum microbiocide to prevent transmission of a large variety of sexually transmitted diseases, is an important advantage.

The Nonoxynol-9 in the present formulation is a spermicide and microbiocide in its own right. It is a nonionic surfactant mixture which can be prepared, for example, by reacting Nonylphenol with Ethelene Oxide. It was first determined to be an effective spermicide agent in approximately 1940. It is a highly stable compound, soluble in water, and is used as a non-ionic surfactant, detergent, emulsifier, wetting agent, dispersant and stablizer.

Since the 1970s, evidence from laboratories has lent support to the prophylactic use of Nonoxynol-9 against some STDs. It has been determined that viral, bacterial and parasitic entities are destroyed in the laboratory under certain conditions, but the compound is very selective. Chlamydia and the candida albicans fungi, for example, are not inhibited. Although gonorrhea and C. trachomatis were observed to respond to Nonoxynol-9 when compared against a placebo, not all of their varieties were destroyed.

Investigation of Nonoxynol-9 against HIV in a number of studies determined that its working mechanism would destroy the free HIV virus, but that this chemical agent was ineffective against virus in cells in male semen. Moreover, although this compound is toxic to many microorganisms, it has little or no effect upon others. For example, Nonoxynol-9 has is ineffective against E. Coli and Staph. aureus, both very serious vaginal intruders.

Thus, with respect to the prevention of AIDS, Nonoxynol-9 is used in the present formulation to disrupt the "free" infectious virus when applied at a non-toxic dosage. It will not however, destroy all viruses, as many viruses are present in cells where Nonoxynol 9's working mechanism does not penetrate. This distinction is an important one, since, when it comes to combatting AIDS, unlike strategies used to fight other human viruses (such as measles virus, poliovirus and hepatitis virus), blocking free-virus entry without removal of the infected cell viruses will not lead to disease prevention.

The second component of the chemical composition, Benzalkonium Chloride, is also a microbiocide and spermicide. It is an active microbiocide against bacteria, some fungi, protozoa, bacterial spores and viruses.

With respect to AIDS, in the present formulation Benzalkonium Chloride has an effective spectrum against the infected cells transferring HIV, in particular, infected cells in male semen. This chemical agent has a direct working mechanical action complementing the activity of Nonoxynol-9. Benzalkonium Chloride's properties allow it to penetrates the cell membranes of a large number of viral and bacterial entities. Once having penetrated, it destroys the metabolic functions of the cell. It destroys the nucleic acids contained in the cells, and specifically the metabolism of DNA, as well as RNA production therein. It further destroys the intracellular enzymes required for cell metabolism. As a result, it is an important second component of the microbiocide composition. In addition to having properties as an active chemical agent, the Benzalkonium Chloride is also used in the formulation as a preservative.

The Povidone Iodine in the present formulation completes the three elements of the microbiocide "triad." In the form commonly encountered, it is an Iodine-Polyvinylpyrriolidone complex. It is a yellowish brown powder fully soluble in water, having a pH of 2.0. Its low pH assists in reducing the total pH of the aqueous chemical microbiocide composition to under 4.0. Furthermore, the Povidone Iodine has an topical anti-infective action that broadens the microbiocide spectrum of the preparation. Povidone Iodine is also an excellent preservative.

In the prior art, Povidone Iodine has been used for pre- and post-operative prepping of operative sites, the treatment of burns, including third-degree burns, and treatment of decubitus and stasis ulcers.

One of its major applications is to provide prompt and soothing symptomatic relief of vaginal irritation, itching and soreness with no irritation to vaginal tissue. It rapidly reduces the aerobic and anaerobic bacteria count, offering comfort from annoying vaginal symptoms and their odor. It is currently used as a treatment for vaginitis conditions, and is used as a cleansing douche. It has a low surface tension with a uniform wetting action which makes it ideal for penetrating into the deep vaginal crypts and crevices. It is active in the presence of blood, pus or vaginal secretions. It is nonirritating to all vaginal mucosa.

Its excellent action as a broad-spectrum microbiocide makes it a useful compound for the disinfection of wounds and for antiseptic treatment of lacerations, abrasions and the disease lesions associated with sexually transmitted disease infections. It destroys both gram-positive and gram-negative bacteria (including antibiotic resistant strains), fungi, protozoa, yeasts and viruses. Its broad spectrum activity covers most commonly occuring skin bacteria.

Its inclusion in the present formulation completes the spectrum of coverage required for STD prevention. Of considerable importance, it is useful against staphylococcus aureus, the entity whose toxins produce toxic-shock syndrome. The Povidone Iodine also provides the preservative required for the solution when encapsulated in a sponge and placed in a hermetically sealed package. The Povidone Iodine further contributes to the present formulations effectiveness as a composition which is microbiocidal, and not merely bacteriostatic.

The need to supplement the working spectrum of Nonoxynol-9 and Benzalkonium Chloride for specifically fungicidal agents, and bacterial agents not within their spectrums, has required addition of this agent. The addition of Povidone Iodine provides free iodine, which is a most useful microbiocide in treating the vaginal infections caused by trichomonas, gonococcus, monilia and chlamydia. This also assists in lowering the incidence of the carcinoma of the cervix, which is now known to be a manifestation of the sexually transmitted papilloma virus, which is destroyed. The iodine content also destroys the highly prevalent genital herpes virus Type-II.

Iodine is a useful bacteriocidal substance because of its non-toxicity when used in low concentrations. There is no bacterial resistance to iodine. Because it has the ability to preform its microbiocide action in the presence of blood, proteins and other vaginal secretions, it provides a total menstrual-cycle protection against STDs.

Consequently, each of the components of the present formulation acts together to form an effective broad spectrum microbiocide, useful in combatting sexually transmitted diseases in general, and AIDS in particular. No cross reactivity between the chemical agents, either inhibiting their effectiveness in combination, or producing unwanted compounds or results, has been observed. Furthermore, the combination has been found to be both safe and non-irritating during use. In combination the toxicity and effects of this chemical composition are safely within the parameters of FDA criteria for an over the counter (OTC) preparation.

Although the levels listed in the table above are those currently preferred, alternative levels for use of these chemical agents are as follows: Nonoxynol-9: 2.0%–8.0%; Benzalkonium Chloride: 0.05%–0.3%; and, Povidone Iodine: 0.15%–2.0%. Although the Benzalkonium levels could be increased to approximately 2.0%, this is not preferred. In an alternate embodiment, Benzethonium Chloride could be substituted for Benzalkonium Chloride at the same levels.

As an active ingredient for use as a spermicide, Benzethonium Chloride is also effective by itself, at these levels, or in combination with Benzalkonium Chloride. Benzethonium Chloride as a spermicide may be used at a preferred level of 0.15%, or in combination with Benzalkonium Chloride at levels of 0.15% for each.

The addition of the Apple Pectin is useful to provide an deodorant function effective in destroying vaginal odor. The Glycine is utilized as a pH reducer which very effectively assists the Povidone Iodine to reduce the Nonoxynol-9 and Benzalkonium Chloride pH levels down to a formula pH of 3.9. The Sodium Carboxymethyl Cellulose is added to increase the viscosity of the solution to create a more stable foaming application.

EXAMPLE 2

Table 2 below sets forth an alternative formulation useful in the invention.

TABLE 2

| Ingredient | Function of Ingredients | Composition % | Mg. |
| --- | --- | --- | --- |
| Nonylphenoxypoly-(Ethyleneoxy)-Ethanol(nonoxynol-9) | Spermicide | 8.000 | 162.50 |
| Benzethonium chloride | Bactericide | 0.150 | 9.75 |

TABLE 2-continued

| Ingredient | Function of Ingredients | Composition % | Mg. |
| --- | --- | --- | --- |
| Pectin | Vaginal Deodorant | 0.500 | 32.50 |
| Glycine | pH adjuster | 0.500 | 32.50 |
| Povidone-Iodine | Bactericide | 0.300 | 19.50 |
| Sodium-Carboxymethyl-cellulose | Swelling agent | 0.160 | 10.40 |
| Distilled Water | Solvent | 95.890 | 6,232.85 |
| TOTAL | | 100.000% | 6,500.00 |

With respect to the constituents of the spermicidal formulation, the nonylphenoxypoly(ethyleneoxy)ethanol is commercially available from a number of producers. All the constituent ingredients of the spermicidal formulation are USP grade and are obtainable from conventional sources.

While the spermicide nonylphenoxypoly(ethyleneoxy)ethanol is exemplified herein, it is not envisioned that this will be the only spermicide utilized by the invention. Other spermicide, such as but not limited to propranolol, alkonium chloride, octoxynol-9; menfetol; dodecaethyleneglycol monolaurate laurethios, methoxypoly-oxyethyleneglycol 550 laurate may also be used.

EXAMPLE 3

Dysmenorrhea Control Therapy (DCT-Sponge)

Dysmenorrhea, or painful menstruation, is the most common of the gynecological disorders. Some degree of painful discomfort is experienced by over half of all women and approximately 10% of these are incapacitated for as much as one to three days each month. The cause of dysmenorrhea is now understood extensively, and has been virtually proven through the use of prostaglandin (PG) synthetase inhibitors.

Primary dysmenorrhea is menstrual pain observed in the absence of any other identifying cause such as pelvic lesions or infection. The pain begins with the onset of menstruation and may last for a few hours or may continue throughout several days. It is of a spasmodic, colicky, labor-like nature, but is sometimes described as severe aching or heaviness in the lower abdomen and the lower back. Nervous symptoms usually accompany the pelvic pain and sometimes nausea, vomiting, diarrhea, headache, and dizziness are experienced. The pain and the accompanying symptoms are primarily reflected during the first day of menstruation and the women may be entirely incapacitated.

The causative factor of this ailment are the cramps created due to exaggerated uterine contractility caused by a hormonal stimulant identified as F 2 (PGF 2a). This hormonal agent is developed during the menstrual cycle in the endometrium where it accumulates and becomes a menstrual stimulant. It is released in the very early stage of menstruation. This causes the uterus receptors to react by contracting the uterine smooth muscle. The endometrial content of this hormone is higher during this secretory stage rather than the follicular phase and is maximum at the point of first menstruation discharge.

Dysmenorrhea is best treated both symptomatically and endocrinological. PG synthetase inhibitors are successful in the management of the disease. A wide assortment of inhibitors may attack the hormonal build-up, and eliminate the potential contraction upon their release. Those women taking oral contraceptives rarely have the symptoms or experience the disease. With inhibition of ovulation, menstrual fluid PG content is suppressed below normal levels. There is suppression of endometrial tissue growth and therefore decreased PG production and its residual discharge volume.

It is highly undesirable to use oral contraceptives for an entire month for the purpose of therapeutic administration for a disease condition. PG inhibition beginning with the day before anticipated menstruation limits the use of drugs and therefore their side effects, unless the contraceptives are otherwise being used to prevent pregnancy.

Management of symptoms once pain begins is through the use of analgesics, sedatives, and other antispasmodic drugs. Diuretics have been employed successfully due to their mobilization of fluid and decrease in pelvic congestion.

The purpose of the DCT-Sponge is to interrupt and inhibit PG accumulations prior to menstruation. Its active ingredient is the PG inhibitor, Ibuprofen. It is the first drug of choice because of its action as a PG inhibitor for dysmenorrhea. It has a longer half-life than most other inhibitors. It is an excellent medium analgesic to eliminate pain and there are relatively few side effects.

By absorbing Ibuprofen through the vaginal cavity all of the gastrointestinal symptoms of rash, blurred vision, nausea, vomiting, and dizziness are eliminated. An advantage of this drug is that it will decrease heavy bleeding and reduce menstrual blood loss. On average the DCT-Sponge will be used for a 6 to 12 hour period prior to anticipated menstruation. Insertion at bedtime the night before will usually provide sufficient absorption of the compound to accomplish the goal of PG inhibition.

Diazepam or Valium may be used to reduce nervousness and tension, relax muscles and encourage sleep. The compounds work rapidly, are long-acting and require a very low dose. Beside being commonly used as an anti-anxiety agent they are also prescribed as muscle relaxants and as sedatives.

A third medicament is Chlorthalidone. This diuretic drug removes excess water from the body and assists in eliminating premenstrual tension. It is a longer acting compound and requires a relatively low dose of active ingredient. Its possible adverse side effects are few.

In combination, these three active ingredients, Ibuprofen, Diazepam and Chlorthalidone with their low dose properties, known effectiveness and low side effect considerations make an unusually good combination for administration 6 to 12 hours prior to the on-set of menstruation to control dysmenorrhea.

The Tampon Foam

The tampon foam is made from a foamable hydrophilic ether polyurethane prepolymer derived from toluene diisocyanate (TDI), toluene diamine (TDA) or other primary aromatic amine. No extractable polyurethane prepolymer less than 50 parts per billion should be present after foam setting.

The foam is formed by using approximately equal weights of prepolymer and water in which other additives may be suspended to create the physical characteristics required, as is well known in the art. The cellular structure and aesthetic properties of the foams produced are controlled by changing surfactants, temperatures or amount of water used, as known in the art.

The surfactants added to the water phase are included to provide for uniform cell structure and better process control. Nonionic water-dispersing surfactants are the additive of choice because of the ease of addition to water and their ability to control cellular structure. A concentration level between 1 and 4% in the aqueous component is effective. For fine size open cells, Pluronic L-62 is used. For reticulated cells having a hydrophilic surface, Pluronic P-65, P-85 or F-127 is used and for fine size reticulated cells, Pluronic F-88 is used. All are available from BASF. For fine cells with a very soft feel, Brij-72 of ICI is used and for other fine cells, fully reticulated providing open cell construction, L-520 of Union Carbide and DC-190 of Dow Corning are used.

The ideal PH of the aqueous phase is 5.0 to 5.5. Long term stability of the final foam product is mandatory because the solvent for the active ingredients is water. There must be no strength loss of the foam structure during storage because the product is intended to have a shelf life greater than 24 months. Freshly made foams are dried by forcing heated air through the cellular structure.

The foam structure is twelve-celled with the membrane of each cell fully reticulated to remove all particles and foam construction debris. The foam has the following specifications:

| | | |
|---|---|---|
| a) Cell count - PPI | 90–100 | (nominal) |
| b) Density - pounds per cubic foot | 2.4 | pounds |
| c) Tensile strength, psi | 22 | pounds |
| d) Elongation percent | 200% | |
| e) Tear Strength lb/inch (minimum) | 4.5 | pounds |
| f) Absorption (Saturation Value) foam weight | 18 to 20 | times |
| g) Sponge Weight | 1.9 | grams |

The foam is in the shape of a truncated sphere as described above.

The Medication

| | Milligrams Per Sponge |
|---|---|
| Ibuprofen U.S.P. - PG Inhibitor | 400 |
| Diazepam - Muscle Relaxant, Antispasmodic | 18 |
| Chlorthalidone - Diuretic | 30 |
| Hydroxypropyl Methyl-Cellulose - Emulsifier Solution Thickener | 60 |
| Pectin - Apple Natural U.S.P. - Deodorant and PH Reducer | 35 |
| Sodium Benzoate - Preservative Antifungal Agent | 10 |
| Ethanol - Solvent | 2,000 |
| Distilled Water | 3,437 |
| Methylparaben - Preservative | 10 |
| Total Product Fill | 6,000 |

The Filled Sponge

The sponge, unfilled, weighs 1.9 grams and the amount of solution which is blocked is 1.9 grams (1900 mg). The total product fill is 6 grams or approximately 30% of saturation value.

Upon entry into the vagina and reaching its seating position, the sponge will release 1 gram of solution. In its seating position and upon removal from the vagina, the sponge can release an additional 3.1 grams (3100 mg) of solution. In total, 4.1 grams of solution can be released upon entry, body action (Kegel exercises) and removal. The releasable amount is about 20% of saturation value.

It is recommended that the sponge be inserted at bedtime or at least 12 hours before anticipated beginning of menstruation.

Packaging

Each sponge is packaged in a sterile humidistatic sealed aluminum foil container. It has a shelf life of no less than three years and is secured from bacterial intrusion by use of appropriate autoclave techniques securing the package.

EXAMPLE 4

Estrogen Replacement Therapy (ERT-Sponge)

The major discomforts and health problems of menopause are directly related to the lack of estrogen level in postmenopausal women. Estrogens and their replacement are the only therapy to protect against osteoporoses, preserve sex life, to keep arteries effective, protect against unrelenting vaginal and urinary track infections and to provide for the relief from devastating hot flashes, insomnia, multiple skin sensations, vaginal itch, and to assist in eliminating depression. Women on estrogen replacement tend to live longer, suffer fewer heart attacks and have one-third the risk of dying from coronary heart disease.

Topical vaginal estrogens are administered via a cream. The estrogens are absorbed by the vaginal tissue. How often a women uses a topical cream depends upon her individual needs.

The major objection by women to the use of estrogen vaginal replacement creams has been the messiness of applying it. Many women object to inserting the cream and others object to the extreme messiness created in both undergarments and bed garments. The time required to clean, sterilize, dry and store the applicator after each application, as long as 15 to 20 minutes, that discourages use.

Because women have used tampons most of their life, a sponge tampon is an ordinary and natural device. It may be applied any time, is not messy, is easily disposable and no other steps need be taken to maintain sterility or to care for an applicator after use.

This reveals a broad base of advantages by utilizing the ERT sponge estrogen replacement therapy.

The Tampon Foam

The foam compound of the filled sponge of the insertion is made as described in Example 3. The foam has the following characteristics.

| | | |
|---|---|---|
| a) Cell count - PPI | 110–130 | (nominal) |
| b) Density - pounds per cubic foot | 2.4 | pounds |
| c) Tensile strength, psi | 22 | pounds |
| d) Elongation percent | 200% | |
| e) Tear Strength lb/inch (minimum) | 4.5 | pounds |
| f) Absorption (Saturation Value) foam weight | 18 to 20 | times |

The tampon is shaped as described in Example 3.

The Medication

Each gram of medicated solution contains 6 mgs. of estradiol U.S.P. This active ingredient is incorporated in a solution having the following composition.

| | Composition % By Weight |
|---|---|
| Distilled Water | 66.1% |
| Isopropyl Alcohol | 30.0% |
| Miscible with water | |
| (a solvent and antiseptic) | |
| Hydroxypropyl Methyl-Cellulose - | 2.0% |
| Emulsifier, whipping thickener to | |
| control viscosity of solution | |
| Propylene Glycol | 0.1% |
| Inhibitor of mold growth, preservative, | |
| disinfectant, humectant solvent | |
| Sodium Phosphate, mono basic | 0.5% |
| A vagina acidifier | |
| Glycerophosphoric Acid | 0.1% |
| A humectant solvent, preservative and | |
| bactericide adjusting pH to 4.5 | |
| Pectin - Apple | 0.5% |
| Natural deodorant | |
| Glycine | 0.5% |
| PH adjuster | |
| Methylparaben | 0.1% |
| Preservative | |
| Sodium Benzoate | 0.1% |
| Preservative | |
| | 100.0% |

The sponge, unfilled weighs 1.9 grams. The amount of solution blocked in the sponge is 2.0 grams. The freely releasable amount of solution is 2.0 grams.

The sponge may be used twice weekly or otherwise as recommended by a physician.

Upon entry into the vagina and reaching its seating position, the sponge will release about 1 gram (1000 mg) of solution. In its seating position and upon removal from the vagina, the sponge can release an additional 1.0 grams (1000 mg) of solution. In total, 2.0 grams of solution can be released upon entry, body action (Kegel exercises) and removal.

EXAMPLE 5

Genital Herpes Therapy (GHT-Sponge)

Genital Herpes is a virus infection creating an extremely common sexually transmitted disease. Over 16 million women are estimated to suffer its consequences in the U.S. It is caused by the herpes simplex virus (HSV, Type 2). The infection is transmitted through sexual contact, and clinical symptoms appear within three to seven days of exposure.

Acyclovir is the only effective anti-viral agent for the treatment of Genital Herpes. It assists in reducing the pain of the primary infection. Time of healing and length of viral shedding is significantly reduced. It also aids in the reduction of recurrent episodes. It is recommended that the medication be used six (6) times a day, starting with the first symptom of infection.

Using an active solution which contains 50 mg of Acyclovir per gram of solution as a topical agent, there has been no reported local intolerance, systemic toxicity, or contact dermatitis. No drug has been detected in blood or urine.

Although most of the prescribed treatments are via oral dosages, the filled sponges of the invention can provide for the topical administration of the active therapeutic. The sponge not only provides for the administration of Acyclovir, but provides for the administration of bactericidal and antiseptic agents to prevent secondary infections.

The advantage of the GHT-Sponge is not only its continued sustained release of active ingredients on a 24 hour basis but the fact that it eliminates the need for applying active ingredients on a three or four hour regimen by the patient herself. It therefore eliminates excessive pain and requires no physical touching of the tissue. The sponge also assists in removing debris and provides the entire vaginal cavity with protection against secondary disease and infection.

The Tampon Foam

| | |
|---|---|
| a) Cell count - PPI | 50–65 (nominal) |
| b) Density - pounds per cubic foot | 2.2 pounds |
| c) Tensile strength, psi | 22 pounds |
| d) Elongation percent | 200% |
| e) Tear Strength lb/inch (minimum) | 4.5 pounds |
| f) Absorption (Saturation Value) | 20 times foam weight |

The Shape of the Sponge

The shape of the sponge is as described in Example 3.

The Medication

The medicated solution in the sponge has the following formula:

| | Milligrams Per Sponge |
|---|---|
| Distilled Water - Solvent | 5,605.0 |
| Acyclovir - Anti-Viral | 400.0 |
| Hydroxypropyl Methyl-Cellulose | 15.0 |
| Emulsifier Solution Thickener | |
| Povidone-Iodine - Bactericide/Fungicide Antiseptic | 30.0 |
| Benzalkonium Chloride | 15.0 |
| Pectin - Apple Natural U.S.P. - Deodorant | 35.0 |
| Ethyl Aminobenzoate - Topical Anesthetic | 400.0 |
| Total Solution Charge per Sponge | 6,500.0 |

The Filled Sponge

The sponge, unfilled, weighs 1.9 grams and the amount of solution which is blocked is 1.9 grams (1900 mg).

Upon entry into the vagina and reaching its seating position, the sponge will release 1 gram of solution. In its seating position and upon removal from the vagina, the sponge can release an additional 3.6 grams (3,600 mg) of solution. In total, 4.6 grams of solution can be released upon entry, body action (Kegel exercises) and removal.

The recommended use is once daily to resolve vaginal conditions.

Packaging

The sponge is packaged as described in Example 3.

EXAMPLE 6

Medicated Vaginal Conditioning Sponges
Bacterial Vaginitis Control—MBVC-S
  Yeast Vaginitis Control—YVC-S
Norman Vaginal Cleansing Control—NVCC-S The human vagina is a natural home for bacteria and yeast cultures. It offers warmth, nourishment and a pH environment conducive to their growth. They are natural inhabitants of the vagina and are necessary to good vaginal health.

When these natural floral cultures are disturbed by invasion of other pathogens or by normal metabolic conditions, a series of vaginal infections may result which create undesirable symptoms such as odorous discharges, irritation, pain, urination pain and itching.

Many of the vaginal infections are passed on among sexual partners and are now incorporated in the term Sexual Transmitted Diseases (STD). Other vaginal infections are created by the imbalance of normal flora caused by the administration of antibiotics, other drug mechanisms, direct intrusion of instruments, illnesses such as diabetes, use of oral contraceptives, self-administration of douches, the use of sits-baths, normal swimming or poor hygiene.

The most frequent intruding vaginal offenders creating the undesirable vaginal symptoms are Trichomonas Vaginalis, Monilia, Candida, Gardnerella, Hemophilus Vaginalis, Herpes Virus (2) and other nonspecific bacterial organisms.

The cure for any bacterial infection is the administration of the appropriate antibiotic. However, because of the frequency and recurrence of Gardnerella, Trichomonas, and other non-specific bacterial organisms, a companion therapy is to increase vaginal acidity. At normal vaginal pH levels of 4.5 to 5.0 these bacterial organisms do not survive. Removal of the debris of vaginal infections is important to relieve irritation.

Medicated Bacterial Vaginitis Control Sponge (MBVC-S)

The Medicated Bacterial Control Sponge (MBVC-S) is designed to provide prompt symptomatic relief of vaginal irritation and soreness. Its active ingredients include a broad spectrum microbicide which significantly and quickly reduces the aerobic and anaerobic bacterial count. The sponge offers the advantage of prolonged medicinal contact by its sustained release of active ingredients upon irritated vaginal tissue, thus providing long-lasting relief.

The sponge uniquely expands the vaginal cavity and simultaneously releases active ingredients into the vaginal crypts and crevasses, thereby assuring complete medication coverage of the tissue area. Its active ingredients continue to penetrate and work in the presence of blood, pus or vaginal secretions. It is virtually non-irritating to vaginal mucosa.

The sponge and the normal vaginal muscular pressure creates a fountain or well of medicaments that swab the cervix with active ingredient. Being placed high in the fornix cavity, it protects against additional intrusion of the infective organism into the uterus or pelvic cavities. Its unique broad-spectrum microbicidal action helps prevent infection by providing a protective film directly upon all vaginal and cervical tissue.

The active ingredients include pH reducers which immediately and effectively reduce the pH level of the vaginal cavity to 4.0. This prevents growth of bacterial invader colonies. In addition to the destruction of gram positive and gram negative bacteria, the active ingredients destroy fungi, viruses, protozoa and yeasts. Its soothing disinfection action upon lacerations and vaginal abrasions provides relief of uncomfortable symptoms. The sponge is best used at bedtime when its active ingredients have an opportunity to work through the night to provide relief of vaginal irritation, itching, and soreness. The sponge also has the ability to remove debris and to absorb pus and other discharges upon removal from the vagina. The sponge is used on a 24 hour basis with seven repeated uses (a new sponge each day) in the first seven days.

Yeast Vaginitis Control Sponge (YVC-S)

This sponge and its active ingredients will cure and control vaginal yeast infections. The main symptom of yeast infection is itching. To cure vaginal yeast infection it is necessary to destroy the yeast cells. The YVC-S does more than just relieve itching, its active ingredients include two effective yeast destroying agents. Its dual action provides prompt non-irritating relief.

The sponge provides for full absorption and removal of yeast debris as well as for the complete expansion of vaginal wall tissue for full application of its active ingredients. Preferably applied at bedtime, its sustained released medicaments continue to flow from its high position seat in the fornix, thus providing for contact of medicament with the cervical cavity and the entire vaginal tissue. A seven day (using a new sponge each day) administration is required even though symptoms may be relieved sooner.

Normal Vagina Cleansing Control Sponge (NVCC-S)

Maintaining vaginal cleanliness does not require douching or spraying of vaginal tissue. In most instances it is contra indicated except where there is a medical purpose.

Many commercial douches, feminine hygiene sprays, and deodorants are irritating and drying and thus add to the possibility of infection. Normal vinegar douches when applied too frequently, although innocent in their purpose, can dry normal vaginal tissue and destroy the mucus balance and the bacterial flora. They can destroy friendly flora which prevent pathogens from multiplying. Physicians have been more concerned about the ill effects of douching, even with just plain warm water, than no douching at all.

The NVCC-Sponge will obviate the need for normal douching and provide a special gentle cleansing formula which will leave women feeling fresh and clean, remove vaginal debris, clear out normal accumulations of vaginal secretions, remove post-sexual deposits and provide a pH reducing additive to lower and maintain the pH level of the vagina at desirable levels.

The sponge provides for complete vaginal cleansing, including the full fornix cavity, by fully expanding and swabbing the entire vaginal tissue. An effective detergent is used for cleansing. The solution is safe and non-irritating to vaginal tissue and provides an antiseptic tissue cleanser which aids in not only reducing the pH level but eliminating inflammatory skin conditions.

The sponge may be retained in the vaginal cavity for a short period of time (15 minutes) and then removed or it can be applied at bedtime in which case its working action will continue for an 8 hour period. The mild antibiotic solution is rapidly effective against Staphylococcus Aureus (the cause of toxic shock syndrome) and is microbicidal against other undesirable biological pathogens.

This sponge also clears out residues from the menstrual period and residues of jellies, creams, suppositories or other contraceptive agents as well as other vaginal secretions and semen debris.

The Sponge

The sponges used for the MBV-S, YVC-S and NVCC-S are prepared as discussed in Example 3. They have the following characteristics.

| | |
|---|---|
| a) Cell count - PPI | 75–85 (nominal) |
| b) Density - pounds per cubic foot | 2.2 pounds |

-continued

| | |
|---|---|
| c) Tensile strength, psi | 22 pounds |
| d) Elongation percent | 200% |
| e) Tear Strength lb/inch (minimum) | 4.5 pounds |
| f) Absorption (Saturation Value) foam weight | 19 to 20 times |

The Shape of the Sponge

The shape of the sponges is as described in Example 3. The weight of each sponge is 2.382 grams.

The Medication

MBVC-SPONGE

The solution has the following formula:

| | Milligrams Per Sponge |
|---|---|
| Distilled Water | 6,325.0 |
| Povidone Iodine - U.S.P. A gram positive and gram negative disinfectant | 30.0 |
| Glycerophosphoric Acid A PH adjuster | 35.0 |
| Pectin - Natural Apple U.S.P. Deodorant | 35.0 |
| Glycine - PH Reducer | 40.0 |
| Hydroxypropyl Methyl-Cellulose Viscosity control Agent | 35.0 |
| Total Solution Fill per Sponge | 6,500.0 |

YVC-SPONGE

The solution has the following formula:

| | Milligrams Per Sponge |
|---|---|
| Clotrimazole - Anti Fungal Agent | 65.0 |
| Distilled Water - Solvent | 6,215.0 |
| Povidone Iodine - Anti Fungal - Bacteria Agent | 30.0 |
| Pectin - Natural Apple - U.S.P. - Deodorant | 35.0 |
| Glycine - PH Reducer | 100.0 |
| Benzalkonium Chloride | 15.0 |
| Hydroxypropyl Methyl-Cellulose Emulsifying Agent - Thickener | 40.0 |
| Total Product Fill per Sponge | 6,500.0 |

NVCC-SPONGE

The solution has the following formula:

| | Milligrams Per Sponge |
|---|---|
| Nonoxynol-9 - Detergent Cleanser | 100.0 |
| Distilled Water - Solvent | 6,275.0 |
| Povidone Iodine - Bactericide/Fungicide | 30.0 |
| Benzalkonium Chloride | 10.0 |
| Pectin - Natural Apple - U.S.P. - Deodorant | 35.0 |
| Glycine - pH Adjuster | 35.0 |
| Hydroxypropyl Methyl-Cellulose | 15.0 |
| Total Solution per Sponge | 6,500.0 |

The Fill

The sponges have an unfilled weight of 1,800 mgs and the amount of blocked solution for each is 1,800 mgs. Upon entry into the vagina and positioning, each will release 1000 mgs of solution. In its seating position and upon removal it can release an additional 3,700 mg. In total each sponge can release 4,700 mg of active solution in the vagina.

The recommended use is as follows:

MBVC-Sponge—One application each day at bedtime, removal in the morning, for seven days.

MBVC-Sponge—One application at bedtime, removal in the morning, for seven days.

NVCC-Sponge—When required, to be used for 20 minutes and removed, or inserted at bedtime and removed the following morning as desired.

Packaging

The sponges are packaged as described in Example 3.

What is claimed is:

1. A chemical composition for administration into the vaginal canal to prevent the transmission of sexually transmitted diseases, said composition comprising:
   (a) Nonylphenoxpoly-(Ethyleneoxy)-Ethanol (Nonoxynol-9);
   (b) Benzalkonium Chloride; and,
   (c) Povidone Iodine.

2. A chemical composition as claimed in claim 1, wherein said Nonylphenoxpoly-(Ethyleneoxy)-Ethanol (Nonoxynol-9) comprises approximately 2.5% of said chemical composition, said Benzalkonium Chloride comprises approximately 0.15% of said chemical composition, and said Povidone Iodine comprises approximately 0.3% of said chemical composition.

3. A chemical composition as claimed in claim 1, wherein said Nonylphenoxpoly-(Ethyleneoxy)-Ethanol (Nonoxynol-9) comprises approximately 2.0–8.0% of said chemical composition, said Benzalkonium Chloride comprises approximately 0.05–2.0% of said chemical composition, and said Povidone Iodine comprises approximately 0.15–2.0% of said chemical composition.

4. A chemical composition as claimed in claim 1, wherein said Nonylphenoxpoly-(Ethyleneoxy)-Ethanol (Nonoxynol-9) comprises 2.0–8.0% of said chemical composition, said Benzalkonium Chloride comprises 0.05–0.3% of said chemical composition, and said Povidone Iodine comprises 0.15–2.0% of said chemical composition.

5. A chemical composition as claimed in claim 1, wherein said composition is located within a vaginal device for placement in the vaginal canal.

6. A chemical composition for administration into the vaginal canal, said composition comprising,
   (a) Nonylphenoxpoly-(Ethyleneoxy)-Ethanol (Nonoxynol-9);
   (b) Benzethonium Chloride; and,
   (c) Povidone Iodine.

7. A chemical composition as claimed in claim 6, wherein said Nonylphenoxpoly-(Ethyleneoxy)-Ethanol (Nonoxynol-9) comprises approximately 2.5% of said chemical composition, said Benzethonium Chloride comprises approximately 0.15% of said chemical composition, and said Povidone Iodine comprises approximately 0.3% of said chemical composition.

8. A chemical composition as claimed in claim 6, wherein said Nonylphenoxpoly-(Ethyleneoxy)-Ethanol (Nonoxynol-9) comprises approximately 2.0–8.0% of said chemical composition, said Benzethonium Chloride comprises approximately 0.05–2.0% of said chemical composition, and said Povidone Iodine comprises approximately 0.15–2.0% of said chemical composition.

9. A chemical composition as claimed in claim 6, wherein said Nonylphenoxpoly-(Ethyleneoxy)-Ethanol (Nonoxynol-9) comprises 2.0–8.0% of said chemical composition, said Benzethonium Chloride comprises 0.05–0.3% of said chemical composition, and said Povidone Iodine comprises 0.15–2.0% of said chemical composition.

10. A chemical composition as claimed in claim 1, wherein said Nonylphenoxpoly-(Ethyleneoxy)-Ethanol (Nonoxynol-9) comprises approximately 2.0–8.0% of said chemical composition.

11. A chemical composition as claimed in claim 1, wherein said Benzalkonium Chloride comprises approximately 0.05–0.3% of said chemical composition.

12. A chemical composition as claimed in claim 1, wherein said Povidone Iodine comprises approximately 0.15–2.0% of said chemical composition.

13. A chemical composition as claimed in claim 6, wherein said Nonylphenoxpoly-(Ethyleneoxy)-Ethanol (Nonoxynol-9) comprises approximately 2.0–8.0% of said chemical composition.

14. A chemical composition as claimed in claim 6, wherein said Benzethonium Chloride comprises approximately 0.05–0.3% of said chemical composition.

15. A chemical composition as claimed in claim 6, wherein said Povidone Iodine comprises approximately 0.15–2.0% of said chemical composition.

16. A chemical composition as claimed in claim 5, wherein said vaginal device comprises a vaginal sponge.

17. A chemical composition as claimed in claim 6, wherein said chemical composition is applied to a vaginal device for placement in the vaginal canal.

18. A chemical composition as claimed in claim 17, wherein said vaginal device comprises a vaginal sponge.

19. A chemical composition as claimed in claim 3, wherein said composition is provided in a vaginal sponge.

20. A method for preventing transmission and spread of a sexually transmitted disease, comprising:
   placing a chemical composition in the vaginal canal, said chemical composition comprising Nonylphenoxpoly-(Ethyleneoxy)-Ethanol, Benzalkonium Chloride, and Povidone Iodine.

21. A method as claimed in claim 20, wherein said Nonylphenoxpoly-(Ethyleneoxy)-Ethanol (Nonoxynol-9) comprises approximately 2.0–8.0% of said chemical composition, said Benzalkonium Chloride comprises approximately 0.05–2.0% of said chemical composition, and said Povidone Iodine comprises approximately 0.15–2.0% of said chemical composition.

22. A method as claimed in claim 20, wherein said chemical composition is provided in a vaginal device for insertion into the vaginal canal.

23. A method as claimed in claim 20, wherein said composition is used for the prevention of Acquired Immunodeficiency Syndrome (AIDS).

24. A method as claimed in claim 20, wherein said sexually transmitted disease is a disease selected from the group consisting of: Acquired Immunodeficiency Syndrome (AIDS), Acute Urethral Syndrome, Bacterial Vaginosis Vulvovaginitis, Candidiasis, Cervical Intraepithelial Neoplasia, Chancroid, Chlamydia, Cytomegalovirus infections, Enteric infections, Genital Warts, Gonorrhea, Granuloma Inguinale, Hepatitis B, Herpes Genitalis, Human Papillomavirus (HPV), Lymphogranuloma venereum (LGV), Molluscum Contagiosum, Mucopurulent Cervicitis, Nongonococcal Urethritis, Pediculosis Pubis, Pelvic Inflammatory Disease (PID), Scabies, Syphilis, Trichomoniasis and Vulvovaginitis.

25. A method for preventing contraception, comprising:
   placing a device in the vaginal canal, wherein said device has a chemical composition applied thereto, said chemical composition comprising spermicidal chemical agents, said chemical agents comprising Benzethonium Chloride.

26. A method as claimed in claim 25, wherein said composition comprises approximately 0.15% of said Benzethonium Chloride.

27. A method as claimed in claim 25, wherein said composition comprises approximately 0.05–2.0% of said Benzethonium Chloride.

* * * * *